(12) United States Patent
Menzenbach et al.

(10) Patent No.: US 6,855,836 B2
(45) Date of Patent: Feb. 15, 2005

(54) 17-METHYLENE STEROIDS, PROCESS FOR THEIR PRODUCTION AND PHARMACEUTICAL COMPOSITIONS THAT CONTAIN THESE COMPOUNDS

(75) Inventors: Bernd Menzenbach, Jena (DE); Peter Droescher, Weimar (DE); Walter Elger, Berlin (DE); Alexander Hillisch, Jena (DE); Gunter Kaufmann, Jena (DE); Hans-Udo Schweikert, Bonn (DE); Gerd Muller, Jena (DE)

(73) Assignee: Jenapharm GmbH & Co. KG, Jena (DE)

( * ) Notice: Subject to any disclaimer, the term of this patent is extended or adjusted under 35 U.S.C. 154(b) by 73 days.

(21) Appl. No.: 09/963,680

(22) Filed: Sep. 27, 2001

(65) Prior Publication Data

US 2002/0091112 A1 Jul. 11, 2002

Related U.S. Application Data

(60) Provisional application No. 60/243,281, filed on Oct. 26, 2000.

(51) Int. Cl.[7] .......................... C07J 13/00; A61K 31/56
(52) U.S. Cl. ...................... 552/526; 552/527; 552/530; 514/169; 514/171; 514/177
(58) Field of Search ................. 552/526, 527, 552/530, 531, 532; 514/169, 171, 177

(56) References Cited

U.S. PATENT DOCUMENTS 2,769,823 A * 11/1956 Schneider et al. ..... 260/397.45
2,789,989 A * 4/1957 Julian et al. ........... 260/397.47
2,802,015 A * 8/1957 Colton ................... 260/397.45
5,194,602 A * 3/1993 Batisi et al. ................. 540/29

OTHER PUBLICATIONS

Barnikol–Oettler et al. (AN CA62:11871e, CAOLD, DN 62:66733, HCAPLUS, abstract of J. Prakt. Chem. (1965), 27(1–2), 18–23).*

AN CA51:18017b, CAOLD, DN 62:66733, HCAPLUS, abstract of US Patent 2802015.*

AN CA51:12161f, CAOLD, abstract of US 2789989.*

.AN CA51:8821c, CAOLD, abstract of US Patent 2769823.*

* cited by examiner

Primary Examiner—Sabiha N. Qazi
(74) Attorney, Agent, or Firm—Millen, White, Zelano & Branigan, P.C.

(57) ABSTRACT

The invention relates to 17-methylene steroids, process for their production and pharmaceutical compositions that contain these compounds.

The compounds according to the invention have a hybrid-type profile of action in the sense that they act as inhibitors of 5α-reductase and simultaneously as gestagens. They are therefore suitable for treating diseases that are the result of elevated androgen levels in certain organs and tissues in men and women. Together with other hormonal substances, such as an estrogen, testosterone or a strong androgen, the compounds according to the invention are suitable as contraceptive agents for women and for men.

25 Claims, No Drawings

17-METHYLENE STEROIDS, PROCESS FOR THEIR PRODUCTION AND PHARMACEUTICAL COMPOSITIONS THAT CONTAIN THESE COMPOUNDS

This application claims the benefit of the filing date of U.S. Provisional Application Ser. No. 60/243,281 filed Oct. 26, 2000.

The invention relates to 17-methylene steroids, process for their production and pharmaceutical compositions that contain these compounds.

The compounds according to the invention have a hybrid-type profile of action in the sense that they act as inhibitors of 5α-reductase and simultaneously as gestagens. They are therefore suitable for treating diseases that are the result of elevated androgen levels in certain organs and tissues in men and women. Together with other hormonal substances, such as an estrogen, testosterone or a strong androgen, the compounds according to the invention are suitable as contraceptive agents for women and for men.

In women, elevated levels of 5α-dihydroprogesterone can contribute to serious feelings of ill-health during the premenstrual syndrome. These disruptions can also be advantageously affected by inhibition of 5α-reductase. The simultaneous presence of a gestagenic action results in an inhibition of gonadal function in males and females. This effect is then desired if an antifertile action or else an inhibition of the hormone secretion of the gonads is to be achieved with the treatment. Since the inhibition of 5α-reductase can irreversibly disrupt the sexual development of the fetus in the case of a woman pregnant with a male fetus, an elimination of fertility accompanied by an antiandrogenic therapy is very desirable. Possible indications are prostate diseases, alopecia of the male type, acne, and hirsutism. The symptoms during the premenstrual syndrome can be alleviated in correspondingly disposed women.

It was found, surprisingly enough, that 17-methylene steroids of general formula I act both as inhibitors of 5α-reductase and as gestagens.

This invention consequently relates to 17-methylene steroids of general formula I

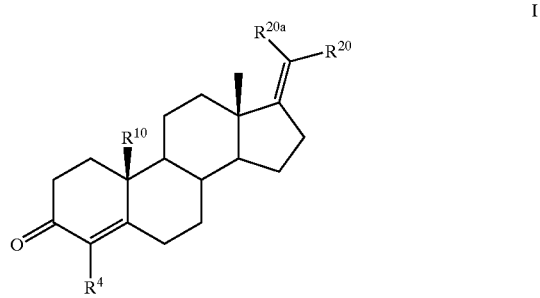

I in which $R^4$ stands for a halogen atom or a pseudohalogen, $R^{10}$ stands for a hydrogen atom or a straight-chain or branched $C_1$-$C_4$ alkyl group, $R^{20}$ and $R^{20a}$, independently of one another, represent a hydrogen atom, a straight-chain or branched $C_{1-4}$ alkyl or hydroxy-$C_{1-4}$ alkyl group, or one of radicals $R^{20}$ and $R^{20a}$ means a hydrogen atom, a straight-chain or branched $C_{1-4}$ alkyl or hydroxy-$C_{1-4}$ alkyl group, and the other radical means a halogen atom or a pseudohalogen.

$R^4$ can mean a halogen atom, such as a fluorine, chlorine, bromine or iodine atom, or a pseudohalogen, such as a cyanate, rhodanid, cyano or azide group, whereby a bromine atom or a cyano group is preferred, and a chlorine atom is especially preferred.

$R^{10}$ can stand for a hydrogen atom or a straight-chain or branched $C_{1-4}$ alkyl group, whereby examples of straight-chain or branched $C_{1-4}$ alkyl groups are methyl, ethyl, propyl, isopropyl, butyl, isobutyl and tert-butyl. $R^{10}$ preferably means a hydrogen atom or a methyl group.

On the one hand, $R^{20}$ and $R^{20a}$, independently of one another, can represent a hydrogen atom, a straight-chain or branched $C_{1-4}$ alkyl or hydroxy-$C_{1-4}$ alkyl group. In this case, $R^{20}$ and $R^{20a}$, independently of one another, preferably mean a hydrogen atom, a methyl group or a group —$CH_2OH$.

In addition, one of radicals $R^{20}$ and $R^{20a}$ can mean a hydrogen atom, a straight-chain or branched $C_{1-4}$ alkyl or hydroxy-$C_{1-4}$ alkyl group, and the other radical can mean a halogen atom, such as a fluorine, chlorine, bromine or iodine atom, or a pseudohalogen, such as a cyanate, rhodanid, cyano or azide group. Examples of straight-chain or branched $C_{1-4}$ alkyl groups are the groups cited for $R^{10}$. Straight-chain or branched hydroxy-$C_{1-4}$ alkyl groups are derived from the above-mentioned straight-chain or branched $C_{1-4}$ alkyl groups, whereby one or more hydrogen atoms are replaced by hydroxy groups.

In this case, one of radicals $R^{20}$ and $R^{20a}$ preferably means a hydrogen atom or a methyl group, and the other radical means a halogen atom, preferably a fluorine atom, especially preferably a chlorine or bromine atom, or a pseudohalogen, preferably an azido or rhodano group, especially preferably a cyano group.

In the case of $R^{20}$ and $R^{20a}$, examples of straight-chain or branched $C_{1-4}$ alkyl groups are the groups that are cited for $R^{10}$. Straight-chain or branched hydroxy-$C_{1-4}$ alkyl groups are derived from these $C_{1-4}$ alkyl groups, whereby one or more hydrogen atoms are replaced by hydroxy groups, such as especially a group —$(CH_2)_n$—OH with n=1 to 4.

Especially preferred are the following compounds:
1) E-17-Chloromethylene-4-chloro-estr-4-en-3-one,
2) E-17-Cyanomethylene-4-chloro-estr-4-en-3-one,
3) Z-17-Cyanomethylene-4-chloro-estr-4-en-3-one,
4) Z-17-(1')-Cyanoethylidene-4-chloro-estr-4-en-3-one,
5) Z-17-Ethylidene-4-chloro-estr-4-en-3-one,
6) E-17-Ethylidene-4-chloro-estr-4-en-3-one,
7) E-17-Bromomethylene-4-chloro-estr-4-en-3-one,
8) Z-17-Chloroethylidene-4-chloro-estr-4-en-3-one,
9) Z-17-Bromoethylidene-4-chloro-estr-4-en-3-one,
10) E-17-Chloromethylene-4-cyano-androst-4-en-3-one,
11) E-17-Chloromethylene-4-chloro-androst-4-en-3-one,
12) E-17-(2')-Hydroxyethylidene-4-chloro-estr-4-en-3-one and
13) Z-17-(2')-Hydroxyethylidene-4-chloro-estr-4-en-3-one.

Subjects of this invention are also pharmaceutical compositions that contain at least one 17-methylene steroid of general formula I as active ingredient, whereby these compositions also contain suitable adjuvants and vehicles, and the use of these compounds for the production of pharmaceutical agents, especially for the indications below.

The compounds according to the invention are suitable for the production of pharmaceutical compositions and preparations. The pharmaceutical compositions or pharmaceutical agents contain as active ingredient one or more of the compounds according to the invention, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., H. V. Czetsch-Lindenwald, Hilfsstoffe für Pharmazie und angrenzende Gebiete [Adjuvants for Pharmaceutics and Related Fields], Pharm. Ind., No. 2, 1961, pages 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor KG, Aulendorf in Württemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc. are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, very frequently oils with or without the addition of a solubilizer, a surfactant, a suspending agent or emulsifier can be used. Examples of oils that are used are olive oil, peanut oil, cottonseed oil, soybean oil, castor oil and sesame oil.

The compounds can also be used in the form of a depot injection or an implant preparation that can be formulated in such a way that a delayed release of active ingredient is made possible.

Implants can contain as inert materials, for example, biodegradable polymers or synthetic silicones such as, for example, silicone gum. In addition, the active ingredients can be added to a patch for percutaneous administration, for example.

For the production of intravaginal systems (e.g., vaginal rings) or intrauterine systems (e.g., pessaries, coils, IUDs, Mirena$^{(R)}$) that are charged with active compounds of general formula I for local administration, various polymers, such as, for example, silicone polymers, ethylenevinyl acetate, polyethylene or polypropylene, are suitable.

To achieve a better bio-availability of the active ingredient, the compounds can also be formulated as cyclodextrin clathrates. In this connection, the compounds are reacted with α-, β- or γ-cyclodextrin or derivatives of the latter (PCT/EP95/02656).

According to the invention, the compounds of general formula I can also be encapsulated with liposomes.

The compounds according to the invention have a hybrid-type profile of action. They are inhibitors of 5α-reductase and, moreover, also act as gestagens. They are therefore suitable for treating diseases that are the result of elevated androgen levels in certain organs and tissues in men and women. In women, elevated levels of 5α-dihydroprogesterone can contribute to serious feelings of ill-health during the premenstrual syndrome. This can be advantageously influenced by inhibition of the 5α-reductase.

The simultaneous presence of a gestagenic action in compounds according to the invention results in an inhibition of gonadal function in males and females. This effect is desirable if an antifertile action or else an inhibition of the hormone secretion of the gonads is to be achieved with the treatment. This is frequently the case in diseases of the prostate (benign prostate hyperplasia). In addition to prostate diseases, possible indications are contraception in both sexes, alopecia of the male type, acne and hirsutism. Together with other hormonal substances, such as an estrogen, testosterone or a strong androgen, the compounds according to the invention are suitable as contraceptive agents for women or for men. In the latter case, the action of testosterone in the prostate by inhibition of the 5α-reductase is reduced, while the gestagenic activity enhances the action in the male gonads, i.e., the inhibition of spermatogenesis.

If the compounds according to the invention are used for female contraception, they can be used by themselves or together with an estrogen. As estrogens, basically all estrogen-active compounds are suitable: estrogens that can be used are, for example, ethinylestradiol, 17β-estradiol as well as its esters, such as estradiol-3-benzoate, estradiol-17-valerate, -cyprionate, -undecylate, -enanthate and/or other estradiol esters (U.S. Pat. Nos. 2,611,773, 2,990,414, 2,054, 271, 2,225,419 and 2,156,599) and conjugated estrogens.

Estradiol-, ethinylestradiol- and estrone-3-sulfamates, for example estrone-N,N-dimethylsulfamate, estrone-N,N-diethylsulfamate, ethinylestradiol-3-N,N-dimethylsulfamate, ethinylestradiol-3-N,N-diethylsulfamate, ethinylestradiol-3-N,N-tetramethylenesulfamate, estrone sulfamate, estradiol-3-sulfamate, estradiol-3-N,N-dimethylsulfamate, estradiol-3-N,N-diethylsulfamate, and ethinylestradiol-3-sulfamate, which produce all prodrugs of the corresponding 3-hydroxy compounds (W. Elger et al., in J. Steroid Biochem. Molec. Biol., Vol. 55, No. 3/4, 395–403, 1995, DE 44 29 398 A1 and DE 44 29 397 A1), can also be used according to the invention.

If the compounds according to the invention are used for male contraception, they can be used by themselves or together with an androgen, such as, for example, testosterone and testosterone esters.

Data for 5α-reductase-type 2-activity in genital dermal homogenates and in vivo data for gestagenic activity are presented by way of example in Tables 1 and 2 below.

TABLE 1

5α-Reductase-Type 2-Activity in Genital Dermal Homogenates under Optimized Conditions at pH 5.5 (IC$_{50}$ (nM))
Progesterone-receptor binding to uterus-cytosol, rabbits, primed
Tracer: 3H-ORG 2058/incubation conditions 0–4° C.; 18 hours
Reference substance: progesterone = 100%

|     | Compound | IC$_{50}$ (nM) | PR Progesterone = 100% |
| --- | --- | --- | --- |
| (1) | E-17-Chloromethylene-4-chloro-estr-4-en-3-one | 250 | 60 |

TABLE 2

In-vivo Data for Gestagenic Activity
Mouse pregnancy maintenance test after s.c. administration

|     | Compound | Dosage mg/animal/day s.c. | Pregnancy rate achieved |
| --- | --- | --- | --- |
| (1) | E-17-Chloromethylene-4-chloro-estr-4-en-3-one | 1.0<br>0.1 | 5/5<br>0/5 |

The data presented in Tables 1 and 2 confirm the hybrid-type profile of action of the compounds according to the invention that act as inhibitors of 5α-reductase and as gestagens.

The 17-methylene steroids of general formula I according to the invention are available from compounds of general formula II (K. Ponsold et al., Pharmazie [Pharmaceutics] 33, 792 (1978)) and general formula V.

The compounds of general formula V are obtained from the corresponding 17α-epoxy compounds (G. Drefahl et al., Ber. 98, 604 (1965)) by reaction with a halide, such as, for example, hydrogen chloride or hydrogen bromide, or pseudohalide, such as, for example, hydrogen thiocyanate or hydrogen nitride, in a dipolar aprotic solvent, preferably DMSO or DMPU.

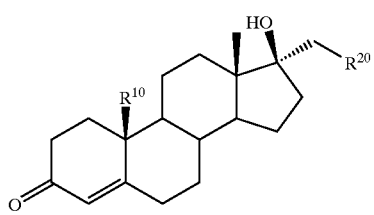

II

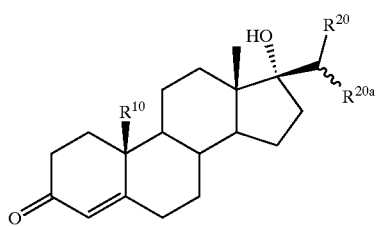

V

The compounds of Formula I are obtained by a compound of general formula II being reacted in an aprotic solvent, preferably in pyridine or triethylamine, with an acid chloride, preferably thionyl chloride or phosphoroxy chloride, to a compound of general formula III,

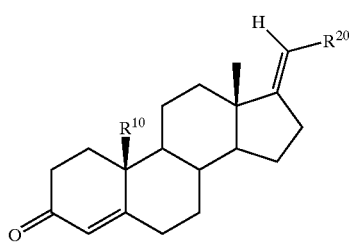

III the latter being subjected in a way that is known in the art to an epoxidation with $H_2O_2$/NaOH in an alcohol, preferably methanol or ethanol, the resulting 4,5-epoxide being opened with nucleophiles, such as halide, such as for example, hydrogen chloride or hydrogen bromide or pseudohalide, such as, for example, hydrogen thiocyanate or hydrogen nitride, in a dipolar aprotic solvent, preferably DMSO or DMPU, dioxane or acetone, to halogen- or pseudohalogen hydrins, and the latter being dehydrated with catalytic mediation by mineral acid, carboxylic acid or sulfonic acid, such as hydrochloric acid, oxalic acid or p-toluenesulfonic acid, in a protic or aprotic solvent, such as methanol or acetone, to a compound of general formula IV

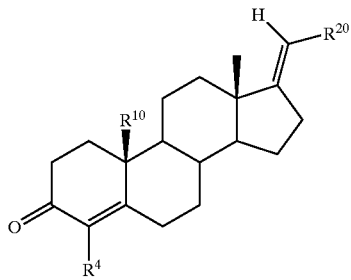

IV in which $R^4$ stands for a halogen atom or pseudohalogen, whereby $R^{10}$ has the above-indicated meaning, and $R^{20}$ means a $C_{1-4}$ alkyl or hydroxy-$C_{1-4}$ alkyl group, a halogen atom or a pseudohalogen.

In addition, 17-methylene steroids of general formula I are obtained by a compound of general formula V being reacted in an aprotic solvent, preferably in pyridine or triethylamine, with an acid chloride, preferably thionyl chloride or phosphoroxy chloride, to a compound of general formula VI

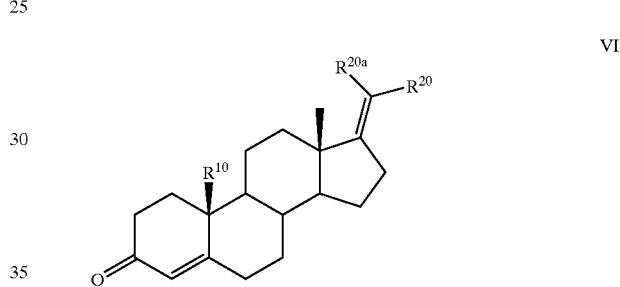

VI the latter being subjected in a way that is known in the art to an epoxidation with $H_2O_2$/NaOH in an alcohol, preferably methanol or ethanol, the resulting 4,5-epoxide being opened with a nucleophile, such as a halide, such as, for example, hydrogen chloride or hydrogen bromide or pseudohalide, such as, for example, hydrogen thiocyanate or hydrogen nitride, in a dipolar aprotic solvent, preferably DMSO or DMPU, dioxane or acetone to a halogen- or pseudohalogen hydrin, and the latter then being dehydrated with catalytic mediation by mineral acid, carboxylic acid or sulfonic acid, such as hydrochloric acid, oxalic acid or p-toluenesulfonic acid, in a protic or aprotic solvent, such as methanol or acetone, to a compound of general formula VII.

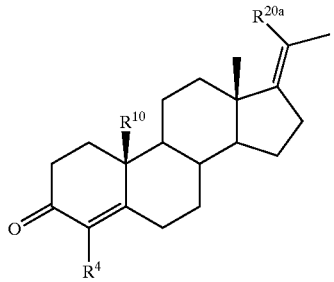

VII

Finally, other 17-methylene steroids of general formula I can be obtained by compounds of general formulas III and VI

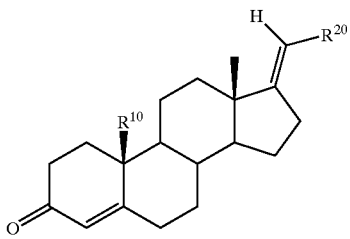

III

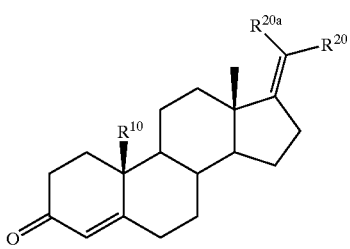

VI being reacted in a way that is known in the art (M. Haase-Held, M. Mattis and J. Mann, J. Chem. Soc. Perkin Trans. 1, 2999, 1992) with $NaIO_4/KMnO_4$ in alcohols, preferably in t-BuOH to the 3,5-seco-keto acids, the latter being converted with $Ac_2O/AcCl$ into unsaturated lactones and the latter being reacted with n-BuLi/$CH_3CN$ in a dipolar aprotic solvent, such as tetrahydrofuran (THF), into compounds of general formulas VIII and IX.

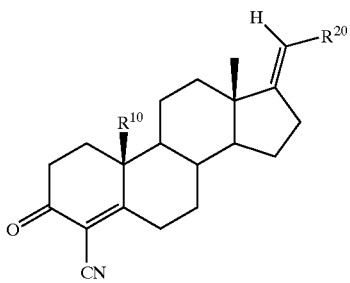

VIII

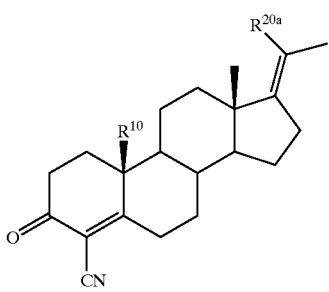

IX

E-17-Chloromethylen-estr-4-en-3-one can also be produced by WITTIG reaction with chloromethyltriphenylphosphonium chloride (S. Miyano et al., J. C. S. Chem. Comm., 446 (1978)). The isomeric 17-cyanomethylen-estr-4-en-3-ones can also be obtained by carbonyl olefination according to HORNER with cyanomethylene diethyl phosphonate or by PETERSON olefination with trimethylsilylacetonitrile (EP-A-0 077 040 or I. Ojima et al., Tetrahedron Lett. 46 (1974) 4005–4008).

Z-20-Cyano-19-norpregna-4,17(20)-dien-3-one is synthesized by PO-activated carbonyl activation with 2-diethylphosphono-propionitrile (R. W. Freerksen et al., Journal American Chemical Society (1977) 1536).

The invention is explained in more detail by the examples below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the foregoing and in the following examples, all temperatures are set forth uncorrected in degrees Celsius and, all parts and percentages are by weight, unless otherwise indicated.

The entire disclosures of all applications, patents and publications, cited, and of corresponding U.S. Provisional Application Ser. No. 60/248,281, filed Oct. 26, 200, is hereby incorporated by reference.

EXAMPLE 1

Z-17-(1'-Chloroethylidene-4-chloro-estr-4-en-3-one

A) Z-17-(1')-Chloroethyliden-estr-4-en-3-one 9.74 mmol (3.28 9) of 17β-(1')-chloroethyl-17-hydroxy-estr-4-en-3-one (see compounds of general formula V) is dissolved in 34 ml of pyridine. While being cooled slightly, 12.66 mmol (0.92 ml) of thionyl chloride is added in drops while being stirred. It is stirred for about 1 hour under a cover gas (argon), and the reaction solution is then added to ice-cooled, dilute hydrochloric acid with a pH=3–4. The sticky precipitation product is extracted with methylene chloride, the combined, neutral-washed extracts are dried with sodium sulfate and concentrated by evaporation. The accumulating solid product is purified by chromatography on silica gel (eluant: toluene/ethyl acetate=95/5) and optionally recrystallization from methanol. 0.6 g of a solid product is obtained.

Flash point=138–141° C.; $[\alpha]_D^{20}=+104°$ (CHCl$_3$)

B) Z-17-(1')-Chloroethylidene-4ξ,5ξ-epoxy-estran-3-one 2.80 mmol (894 mg) of Z-17-(1'-(chloroethyliden-estr-4-en-3-one is dissolved in a mixture of 9 ml of methanol and 7.3 ml of methylene chloride and cooled to 0° C. 6.31 mmol (0.63 ml) of hydrogen peroxide (30%) and 1.26 mmol (0.3 ml) of sodium hydroxide solution (c=4 mol/l) are added in drops in succession to the cooled solution while being stirred and under a cover gas (argon). After dropwise addition is completed, the temperature is slowly increased to room temperature. After about 1.5 hours of reaction time, the mixture is added to ice water and then extracted with methylene chloride. The combined extracts are dried with sodium sulfate and concentrated by evaporation. 926 mg of a light yellow solid is obtained.

$^1$H-NMR/δ (CDCl$_3$/ppm) 0.94(18-H), 1.99(21-H), 3.04 (4-H)

C) Z-17-(1')-Chloroethylidene-4-chloro-estr-4-en-3-one 2.71 mmol (896 mg) of Z-17-(1')-chloroethyliden-4ξ,5ξ, epoxy-estran-3-one is dissolved in 25 ml of 1,3-dimethyltetrahydro-2(1H)-pyrimidinone (DMPU), and 26.54 mmol (2.2 ml) of hydrochloric acid (37%) is slowly added in drops. After 1 hour of stirring under a cover gas (argon), the reaction solution is added to ice-cooled, aqueous sodium bicarbonate solution, the precipitation is suctioned off, and it is finally dried in a desiccator with potassium hydroxide. By flash-chromatography on silica gel (eluant: toluene/ethyl acetate=99/1) and subsequent recrystallization from methanol/acetone, 353 mg of solid product is obtained.

Flash point=182–185° C.; $[\alpha]_D^{20}=+137°$ (CHCl$_3$)

EXAMPLE 2

Z-17-(1')-Bromoethylidene-4-chloro-estr-4-en-3-one

Starting from 17β-(1')-bromoethyl-17-hydroxy-estr-4-en-3-one (see compounds of general formula V), Z-17-(1')- bromoethylidene-4-chloro-estr-4-en-3-one is obtained analogously to 17β-(1')-chloroethyl-estr-4-en-3-one.

Flash point=164–173° C.; $[\alpha]_D^{20}$=+138° (CHCl$_3$)

EXAMPLE 3

E-17-Chloromethylene-4-chloro-estr-4-en-3-one
A) E-17-Chloromethylen-estr-4-en-3-one 18.27 mmol (5.9 g) of 17α-chloromethyl-17-hydroxy-estr-4-en-3-one is dissolved in 60 ml of pyridine. While being cooled slightly, 21.9 mmol (1.56 ml) of thionyl chloride is added in drops while being stirred. It is stirred under a cover gas (argon) for about 1 hour, and the reaction solution is then added to ice-cooled, dilute hydrochloric acid with a pH=3–4. The sticky precipitation product is extracted with methylene chloride, the combined, neutral-washed extracts are dried on sodium sulfate and concentrated by evaporation. The accumulating solid product is purified by chromatography on silica gel (eluant: n-hexane/ethyl acetate=85/15). After recrystallization from acetone, 1.6 g of product is obtained.

Flash point=143–146° C.; $[\alpha]_D^{20}$=+20° (CHCl$_3$)
B) E-17-Chloromethylene-4ξ,5ξ-epoxy-estran-3-one 3.93 mmol (1.2 9) of E-17-chloromethylen-estr-4-en-3-one is dissolved in a mixture of 12 ml of methanol and 10 ml of methylene chloride under a cover gas (argon) and cooled to 0° C. 9.2 mmol (0.94 ml) of hydrogen peroxide (30%) and 1.65 mmol (0.4 ml) of sodium hydroxide solution (c=4 mol/l) are added in drops in succession to the cooled solution while being stirred. After dropwise addition is completed, the temperature is slowly increased to room temperature. After about 1.5 hours of reaction time, the mixture is added to ice water and extracted with methylene chloride. The combined extracts are dried on sodium sulfate and concentrated by evaporation. 1.1 g of a white, sticky foam is obtained.

$^1$H-NMR/δ (CDCl$_3$/ppm) 0.87(18-H), 3.04(4-H), 5.70 (20-H)
C) E-17-Chloromethylene-4-chloro-estr-4-en-3-one 3.42 mmol (1.1 g) of E-17-chloromethylene-4ξ,5ξ-epoxy-estran-3-one is dissolved in 26 ml of DMPU, and 33 mmol (2.74 ml) of hydrochloric acid (37%) is slowly added in drops. After 1 hour, the reaction solution is added to ice-cooled, aqueous sodium bicarbonate solution, the precipitation is suctioned off and dried in a desiccator on potassium hydroxide. After recrystallization from acetone, 760 mg of white crystals is obtained.

Flash point=182–194° C.; $[\alpha]_D^{20}$=+63° (CHCl$_3$)

EXAMPLE 4

E-17-Bromomethylene-4-chloro-estr-4-en-3-one

Starting from E-17-bromomethyl-17β-hydroxy-estr-4-en-3-one (see compounds of general formula II), E-17-bromomethylene-4-chloro-estr-4-en-3-one is obtained analogously to 17α-chloromethyl-17-hydroxy-estr-4-en-3-one.

Flash point=169–176° C.; $[\alpha]_D^{20}$=+45° (CHCl$_3$)

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:
1. A 17-Methylene steroid of formula I

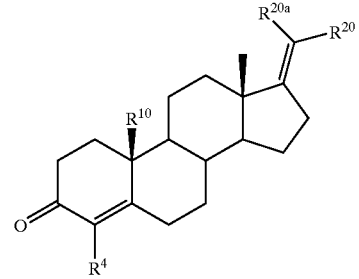

in which
  $R^4$ is a halogen atom or a pseudohalogen,
  $R^{10}$ is a hydrogen atom or a straight-chain or branched $C_1$–$C_4$ alkyl group,
  $R^{20}$ and $R^{20a}$ are, independently of one another, a straight-chain or branched $C_{1-4}$ alkyl or hydroxy-$C_{1-4}$ alkyl group, or
  one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen.

2. A 17-Methylene steroids according to claim 1, wherein $R^4$ is a chlorine or bromine atom or a cyano group.

3. A 17-Methylene steroid of formula I

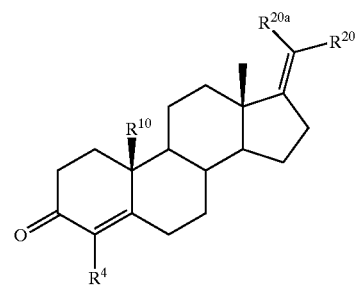

in which
  $R^4$ is a halogen atom or a pseudohalogen,
  $R^{10}$ is a hydrogen atom or a straight-chain or branched $C_1$–$C_4$ alkyl group,
  one of radicals $R^{20}$ and $R^{20a}$ is a hydrogen atom or a methyl group, and the other radical is a fluorine, chlorine or bromine atom, an azido, cyano or rhodano group or hydroxymethyl.

4. A 17-Methylene steroids according to claim 1, wherein $R^{10}$ is a hydrogen atom or a methyl group.

5. A 17-Methylene steroid selected from the group consisting of
  1) E-17-Chloromethylene-4-chloro-estr-4-en-3-one,
  2) E-17-Cyanomethylene-4-chloro-estr-4-en-3-one,
  3) Z-17-Cyanomethylene-4-chloro-estr-4-en-3-one,
  4) Z-17-(1')-Cyanoethylidene-4-chloro-estr-4-en-3one,
  5) Z-17-Ethylidene-4-chloro-estr-4-en-3-one,
  6) E-17-Ethylidene-4-chloro-estr-4-en-3-one,
  7) E-17-Bromomethylene-4-chloro-estr-4-en-3-one,
  8) Z-17-Chloroethylidene-4-chloro-estr-4-en-3-one,
  9) Z-17-Bromoethylidene-4-chloro-estr-4-en-3-one, 10) E-17-Chloromethylene-4-cyano-androst-4-en-3-one,
11) E-17-Chloromethylene-4-chloro-androst-4-en-3-one,
12) E-17-(2')-Hydroxyethylidene-4-chloro-estr-4-en-3-one, and
13) Z-17-(2')-Hydroxyethylidene-4-chloro-estr-4-en-3-one.

6. A process for preparing a 17-methylene steroid of formula I

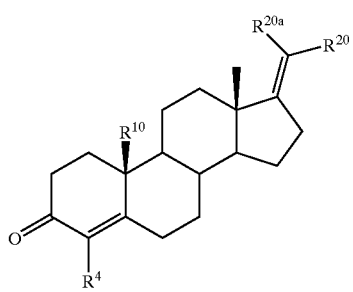

I in which $R^4$ is a halogen atom or a pseudohalogen, $R^{10}$ is a hydrogen atom or a straight-chain or branched $C_1$–$C_4$ alkyl group, $R^{20}$ is a hydrogen atom, a straight-chain or branched $C_{1-4}$ alkyl or hydroxy-$C_{1-4}$ alkyl group, or a halogen atom or a pseudohalogen, and $R^{20a}$ is a hydrogen atom, comprising reacting a compound of formula II,

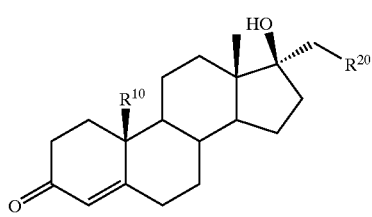

II in an aprotic solvent with an acid chloride to form a 17-methylene steroid of formula III,

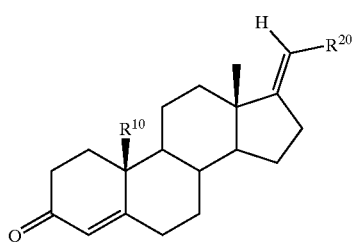

III the 4,5-epoxide is generated with $H_2O_2$/NaOH, the 4,5-epoxide is then opened with a nucleophilic reagent, which is derived from a halogen atom or pseudohalogen, in a dipolar aprotic solvent to a halogen- or pseudohalogen hydrin, and optionally reacted with mineral acid, carboxylic acid or sulfonic acid in a protic or aprotic solvent with dehydration to a compound of formula IV,

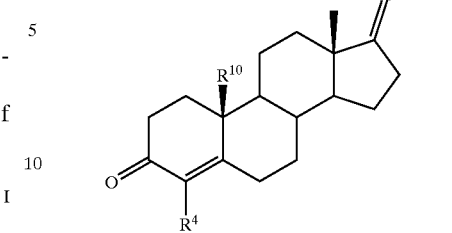

IV wherein $R^4$ is a halogen atom or pseudohalogen, $R^{10}$ is a hydrogen atom or a straight-chain or branched $C_1$–$C_4$ alkyl group, and $R^{20}$ is a $C_{1-4}$ alkyl or hydroxy-$C_{1-4}$ alkyl group, a halogen atom or a pseudohalogen.

7. A process for preparing a 17-methylene steroid of formula I

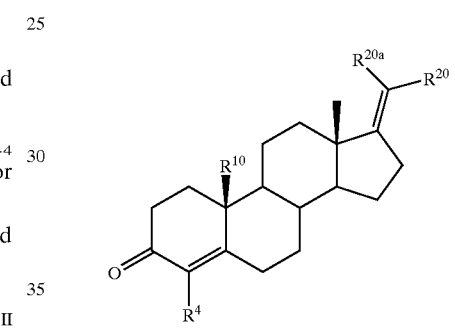

I in which $R^4$ is a halogen atom or a pseudohalogen, $R^{10}$ is a hydrogen atom or a straight-chain or branched $C_1$–$C_4$ alkyl group, $R^{20}$ and $R^{20a}$ are, independently of one another, a hydrogen atom, a straight-chain or branched $C_{1-4}$ alkyl or hydroxy-$C_{1-4}$ alkyl group, or one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen, comprising reacting a compound of formula V,

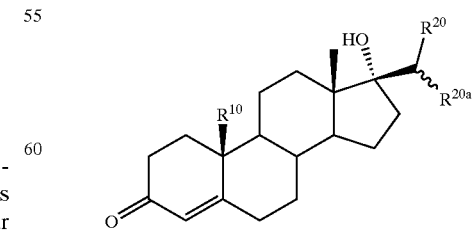

V with an acid chloride in an aprotic solvent to form a methylene steroid of formula VI,

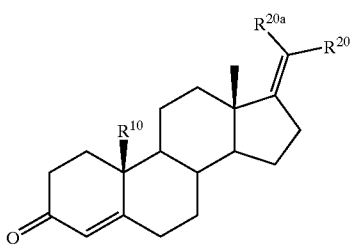

the 4,5-epoxide is generated with $H_2O_2$/NaOH, the 4,5-epoxide is then opened with a nucleophilic reagent, which is derived from a halogen atom or pseudohalogen, in a dipolar aprotic solvent to a halogen- or pseudohalogen hydrin, and optionally reacted with mineral acid, carboxylic acid or sulfonic acid in a protic or aprotic solvent with dehydration to a compound of formula VII,

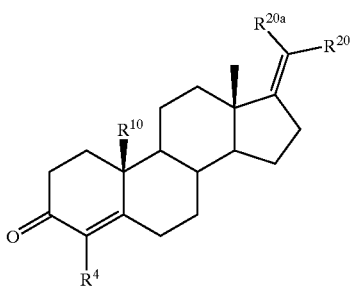

in which $R^4$ is a halogen atom or pseudohalogen, $R^{10}$ is a hydrogen atom or a straight-chain or branched $C_1$–$C_4$ alkyl group, and $R^{20}$ is a $C_{1-4}$ alkyl or hydroxy-$C_{1-4}$ alkyl group, and $R^{20a}$ is a hydrogen atom, a halogen atom or a pseudohalogen.

8. A 17-methylene steroid of formula I

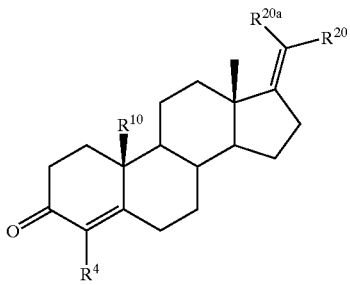

in which $R^4$ is a halogen atom or a pseudohalogen, $R^{10}$ is a hydrogen atom or an ethyl, propyl, isopropyl, butyl, isobutyl, or tert-butyl group, $R^{20}$ and $R^{20a}$ are, independently of one another, a hydrogen atom, a straight-chain or branched $C_{1-4}$ alkyl or hydroxy-$C_{1-4}$ alkyl group, or one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen, and a pharmaceutically compatible adjuvant or vehicle.

9. A 17-Methylene steroid of formula I

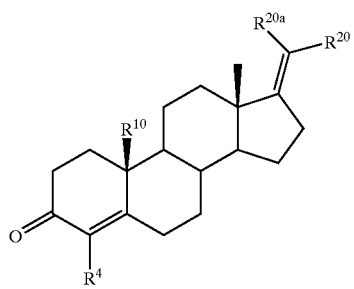

in which $R^4$ is a fluorine, bromine, or iodine atom or a pseudohalogen, $R^{10}$ is a hydrogen atom or a straight-chain or branched $C_1$–$C_4$ alkyl group, $R^{20}$ and $R^{20a}$ are, independently of one another, a hydrogen atom, a straight-chain or branched $C_{1-4}$ alkyl or hydroxy-$C_{1-4}$ alkyl group, or one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen.

10. A 17-Methylene steroid of formula I

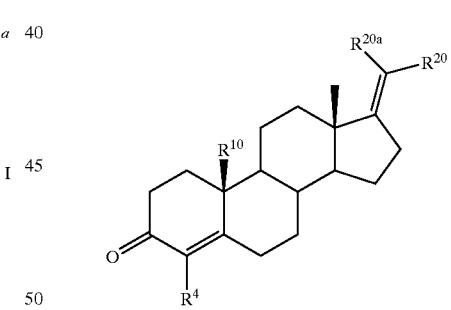

in which $R^4$ is a halogen atom or a pseudohalogen, $R^{10}$ is a hydrogen atom or a straight-chain or branched $C_1$–$C_4$ alkyl group, $R^{20}$ is a hydrogen atom, a straight-chain or branched $C_{1-4}$ alkyl or hydroxy-$C_{1-4}$ alkyl group, $R^{20a}$ is a straight-chain or branched $C_{1-4}$ alkyl or hydroxy-$C_{1-4}$ alkyl group, or one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen.

11. A 17-Methylene steroid of formula I

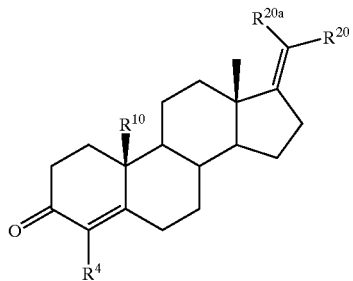

in which
- $R^4$ is a pseudohalogen,
- $R^{10}$ is a hydrogen atom or a straight-chain or branched $C_1$–$C_4$ alkyl group,
- $R^{20}$ and $R^{20a}$ are, independently of one another, a hydrogen atom, a straight-chain or branched $C_{1-4}$ alkyl or hydroxy-$C_{1-4}$ alkyl group, or
- one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen.

12. A pharmaceutical composition comprising at least one 17-methylene steroid according to claim 8 and a pharmaceutically compatible adjuvant or vehicle.

13. A 17-Methylene steroid of formula I

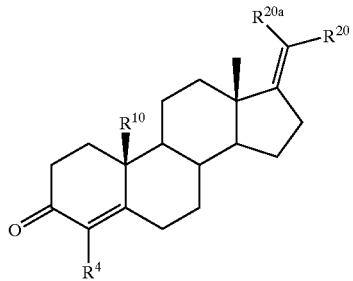

in which
- $R^4$ is an azido, rhodano or cyano group,
- $R^{10}$ is a hydrogen atom or a straight-chain or branched $C_1$–$C_4$ alkyl group,
- $R^{20}$ and $R^{20a}$ are, independently of one another, a hydrogen atom, a straight-chain or branched $C_{1-4}$ alkyl or hydroxy-$C_{1-4}$ alkyl group, or
- one of radicals $R^{20}$ and $R^{20a}$ is a hydrogen atom, a straight-chain or branched $C_{1-4}$ alkyl or hydroxy-$C_{1-4}$ alkyl group, and the other radical is a halogen atom or a pseudohalogen.

14. A pharmaceutical composition comprising at least one 17-methylene steroid according to claim 1 and a pharmaceutically compatible adjuvant or vehicle.

15. A pharmaceutical composition comprising at least one 17-methylene steroid according to claim 9 and a pharmaceutically compatible adjuvant or vehicle.

16. A pharmaceutical composition comprising at least one 17-methylene steroid according to claim 10 and a pharmaceutically compatible adjuvant or vehicle.

17. A pharmaceutical composition comprising at least one 17-methylene steroid according to claim 11 and a pharmaceutically compatible adjuvant or vehicle.

18. A pharmaceutical composition comprising at least one 17-methylene steroid according to claim 5 and a pharmaceutically compatible adjuvant or vehicle.

19. A method of treating a prostate disease comprising administering to a patient in need thereof an effective amount of a compound according to claim 5 or a pharmaceutical composition comprising said effective amount of said compound and a pharmaceutical compatible adjuvant or vehicle.

20. A method of effecting contraception in a man or in a woman comprising administering to a patient in need thereof an effective amount of a compound according to claim 5 or a pharmaceutical composition comprising said effective amount of said compound and a pharmaceutical compatible adjuvant or vehicle.

21. A method inhibiting 5α-reductase comprising administering to a patient in need thereof an effective amount of a compound according to claim 5.

22. A 17-Methylene steroid according to claim 1, wherein $R^4$ is a halogen atom.

23. A 17-Methylene steroid according to claim 1, wherein $R^4$ is an azido, rhodano or cyano group.

24. A 17-Methylene steroid according to claim 1, wherein $R^4$ is a cyano group.

25. A 17-Methylene steroid of formula I

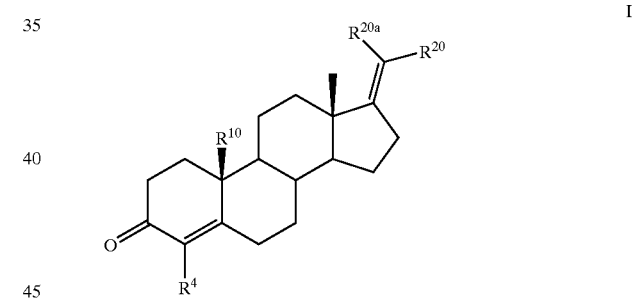

in which
- $R^4$ is a halogen atom or a pseudohalogen,
- $R^{10}$ is a hydrogen atom or a straight-chain or branched $C_1$–$C_4$ alkyl group,
- one of $R^{20}$ or $R^{20a}$ is a hydrogen atom, a straight-chain or branched $C_{1-4}$ alkyl or hydroxy-$C_{1-4}$ alkyl group, and the other of
- $R^{20}$ or $R^{20a}$ is a straight-chain or branched $C_{1-4}$ alkyl, a hydroxy-$C_{1-4}$ alkyl group, a halogen atom or a pseudohalogen.

* * * * *